United States Patent [19]
Kishi

[11] Patent Number: 5,476,090
[45] Date of Patent: Dec. 19, 1995

[54] HARD ENCLOSURE AND SHEATH FOR SAME

[75] Inventor: Yukitoshi Kishi, Saitama, Japan

[73] Assignee: Fuji Photo Optical Co., Ltd., Omiya, Japan

[21] Appl. No.: 92,086

[22] Filed: Jul. 12, 1993

[30] Foreign Application Priority Data

Jul. 15, 1992 [JP] Japan ................................ 4-210982
Jul. 15, 1992 [JP] Japan ................................ 4-210983
Jul. 24, 1992 [JP] Japan ................................ 4-218295

[51] Int. Cl.⁶ .................................................. A61B 1/00
[52] U.S. Cl. ..................... 600/121; 604/263; 600/138; 600/131
[58] Field of Search .................... 128/4, 6, 917, 128/918, 919, 844, 4, 6; 604/263

[56] References Cited

U.S. PATENT DOCUMENTS

| 4,878,485 | 11/1989 | Adair | 128/4 |
| 4,974,580 | 12/1990 | Anapliotis | 128/4 |
| 5,168,863 | 12/1992 | Kurtzer | |
| 5,237,984 | 8/1993 | Williams, III et al. | 604/263 X |

*Primary Examiner*—Richard J. Apley
*Assistant Examiner*—Beverly A. Meindl
*Attorney, Agent, or Firm*—Jordan & Hamburg

[57] ABSTRACT

The sheath according to the present invention comprises the hard sheath member which can cover the entire hard insertion tube of the hard endoscope and the soft sheath member. So, when the hard insertion tube is inserted into the body cavity of a patient, it will not possibly be contaminated with the blood, bacteria or the like. The hard insertion tube can be used for a next endoscopy without the necessity of sterilization or disinfection. Also according to the present invention, the soft sheath member is fitted closely over the controller, so that the controller can be operated from outside the soft sheath member without any direct contact with the controller. The controller may not be sterilized or disinfected for a next use of the hard endoscope.

12 Claims, 7 Drawing Sheets

HARD ENCLOSURE AND SHEATH FOR SAME

BACKGROUND OF THE INVENTION

The present invention relates to a hard endoscope of which the hard insertion tube provided at the end of its controller is inserted into the body cavity of a patient through a trocar for viewing the cavity inside and for other purposes such as removal of tissues or secretions for biopsy, photography, air or water filling and the like, and to a sheath destined for use as attached on the hard endoscope.

Figure 1:
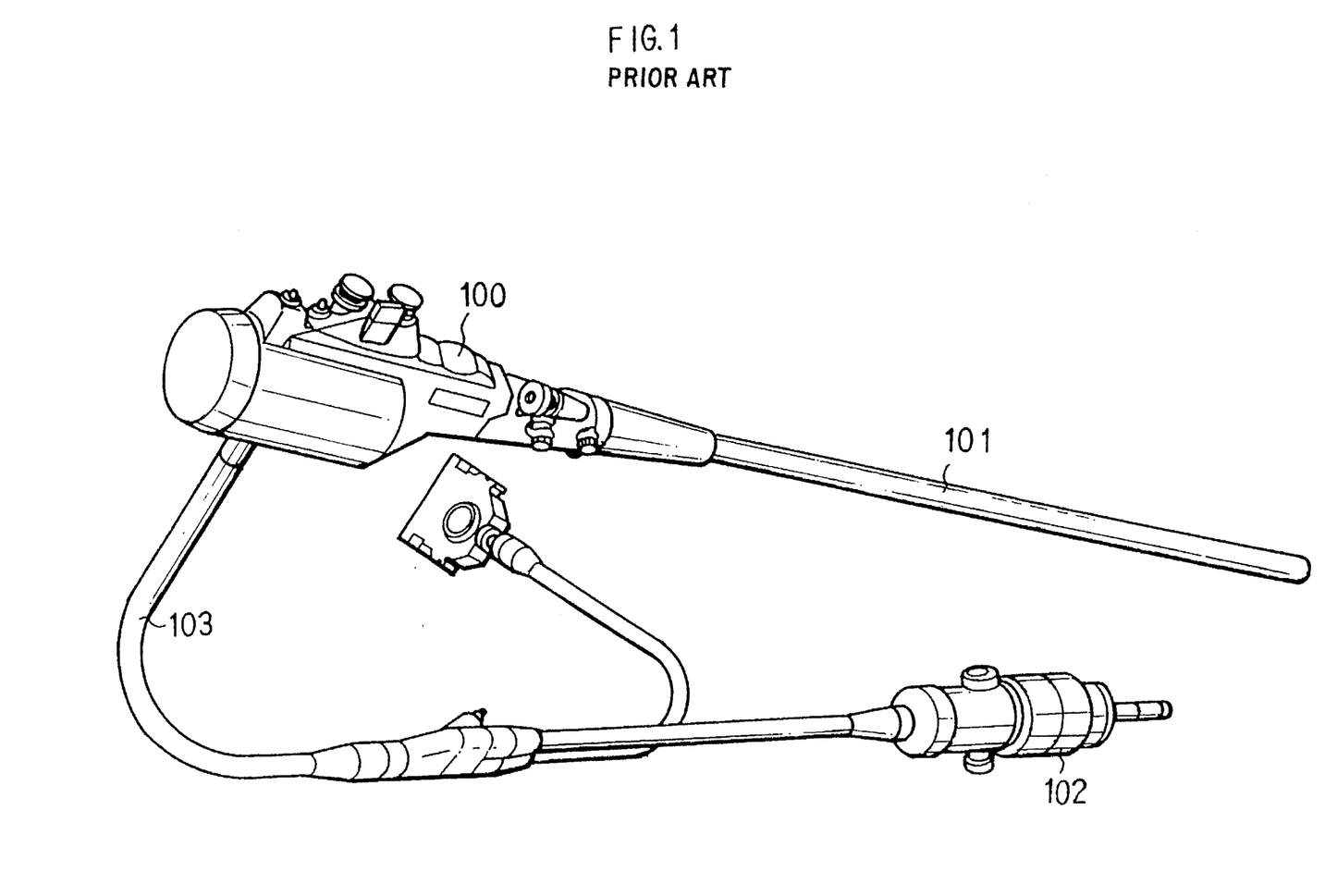
FIG. 1 is a perspective view of a conventional endoscope.

Heretofore, various types of hard endoscopes have been proposed. A typical hard endoscope is known which comprises, as shown in FIG. 1, a controller 100, having control buttons and which is operated as held in hand by the operator, a hard insertion tube 101 provided at the end of the controller 100 as connected to the latter and which is to be inserted into a patient's body cavity through a trocar (not shown), and a coupling tube 103 which is to be connected to a necessary light source by means of a connector 102 and to which an external apparatus (not shown) such image signal processing unit or the 1 ire is to be connected where the endoscope is an electrical one having a charge coupled device (CCD) disposed at the front end of the hard insertion tube 101 or an external apparatus (not shown) such as a camera or video tape recorder (VTR) is to be connected.

Generally in such an endoscope, the coupling tube 103 is fixed to the endoscope body and extended laterally from the controller 100 and almost perpendicularly thereto.

When handling such hard endoscope, the operator has to turn the endoscope body about the axis of the controller 100 for the convenience of operation, for example, because of his position in relation to the patient. In this case, the coupling tube 103 will be turned along with the controller 100. An external apparatus connected to the coupling tube 103 will be displaced or the coupling tube 103 will hit the patient or operator. Also an excessive force will be applied to between the coupling tube 103 and controller 100, possibly causing failure of the endoscope.

Further, the hard endoscope is contaminated with blood or other because it is inserted into the patient's body, and so it must be subjected to sterilization or disinfection before a next endoscopy. It is sterilized in a gas, for example, EOG (ethylene oxide gas).

However, since the insertion tube of the hard endoscope is thin and long and has small-diameter passages formed longitudinally therein, that is, it has a complicated internal structure, the sterilization or disinfection requires extensive labor and time.

To save such labor and time for sterilization or disinfection, an endoscope sheath was proposed as disclosed in, for example, the Japanese Examined Patent Publication No. 2-54734. This endoscope sheath consists of a hard support having the form of a cylindrical cap, and a soft cylinder made of an elastomer or the like and wound like a roll on the hard support. This sheath is to be used as fitted on the portion of the insertion tube of the endoscope.

However, the sheath of such a structure is fitted on a short end portion of the insertion tube of the endoscope. In other words, the sheath covers only a limited length of the insertion tube portion that is inserted into the patient's body, and so the insertion tube portion left not covered by the sheath still has to be sterilized or disinfected.

For simplifying such troublesome and labor intensive sterilization or disinfection, it has been proposed to entirely cover, with a sheath, a portion of such an endoscope, which is likely to transfer its contamination to a next patient subject to an endoscopy, including the controller which the operator touches with his fingers. However, because the buttons that project at the controller, the and coupling tube extending laterally and nearly perpendicularly, etc. interfere with such full covering and for the following reasons, this sheath could not have been put into pratical utilization.

Namely, if made of a material having a large coefficient of friction such as elastomer, the soft portion of the sheath, that is to be inserted into the abdominal cavity or the like through a trocar, cannot smoothly be passed through the trocar because of its great coefficient of friction.

To avoid this, a space may be provided between the soft portion and trocar. However, as the soft portion has to keep an airtightness with respect to the trocar, the dimension of the space between the outer surface of the soft portion and the inner wall of the trocar is strictly limited. Thus, such spacing is impossible in practice. Furthermore, even if the soft portion can be passed through the trocar, a blade, if any, provided at the end of the trocar would cut and break the soft portion.

SUMMARY OF THE INVENTION

Accordingly, it is an object of the present invention to overcome the drawbacks of the prior art by providing a hard endoscope on which the a sheath can be put easily and smoothly and of which the control buttons can be operated from above the sheath.

The present invention has another object to provide a sheath for a hard endoscope, of which the airtightness with respect to the trocar of the endoscope can be ensured and which cannot be damaged or broken by a blade provided on the trocar.

The above object is accomplished by providing a hard endoscope comprising, a hard insertion tube which is to be inserted into the body cavity of a patient through a trocar, a controller provided as connected to the hard insertion tube, a coupling tube for connection of an external apparatus, and a sheath consisting of hard and soft sheath members, wherein the controller is designed to have the form of a smooth curved profile, the controller, hard insertion tube and coupling tube are adapted to have a nearly linear form when assembled together, control buttons for controlling the external apparatus and so forth are disposed so as not to project from the outer surface of the controller, the hard sheath member of which the inner and outer surfaces are smooth is fitted on the hard insertion tube and the soft sheath member is attached on the controller so that the control buttons are to be operated from outside the soft sheath member.

Also the above object is accomplished by providing a hard endoscope having a hard insertion tube to be inserted into the body cavity of a patient through a trocar, a controller and a coupling tube for connection of an external apparatus, the tube, controller and coupling tube being disposed so as to have a nearly linear form when assembled together, and in which a hard sheath member of a sheath is fitted on the hard insertion tube and a soft sheath member of the sheath is attached on the controller, wherein a means of positioning the sheath circumferentially of the endoscope is provided between the hard sheath member and the controller or hard insertion tube of the hard endoscope.

Further the above object is accomplished by providing a sheath for use as fitted on a hard endoscope having a hard insertion tube to be inserted into the body cavity of a patient through a trocar, a controller having a concavity in which control buttons are disposed so as not to outwardly project and a coupling tube for connection of an external apparatus, the tube, controller and coupling tube being disposed so as to have a generally linear form when assembled together, comprising a hard sheath member made of a hard material, formed to have a constant outside diameter so that an airtightness can be maintained during insertion of the hard insertion tube into the trocar and which has the inner and outer circumferential surfaces worked so as to be free from irregularity thereon, and an expansible soft sheath member removably attachable at the open end of the hard sheath member and fitted on the controller of the hard endoscope.

DETAILED DESCRIPTION OF THE PREFERRED EMBODIMENT

One embodiment of the present invention will be discussed with reference to the drawings.

Figure 2:
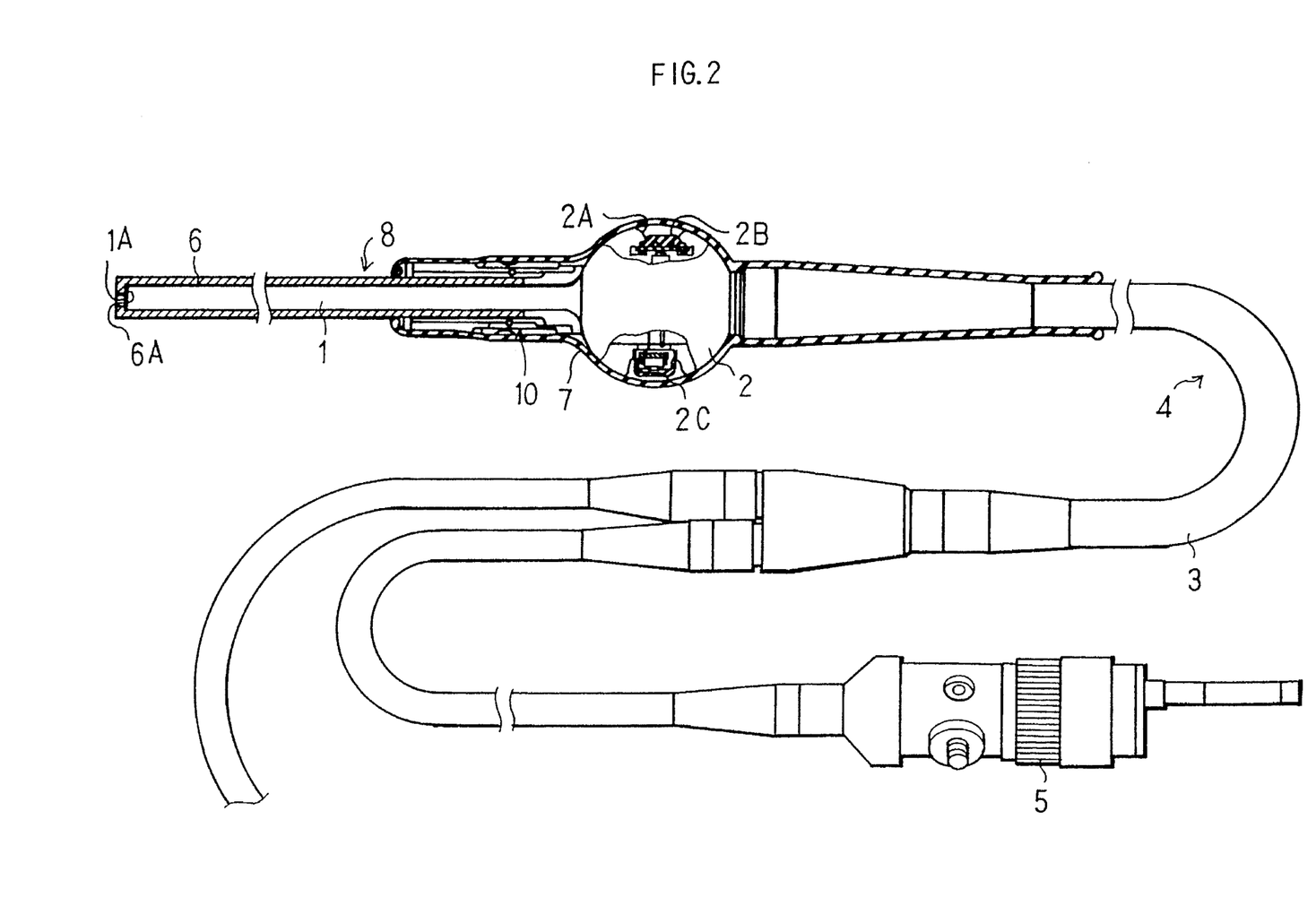
FIG. 2 is a partially sectional and fragmentary schematic view of the hard endoscope according to the present invention, showing the sheath attached on the endoscope.
Figure 7:
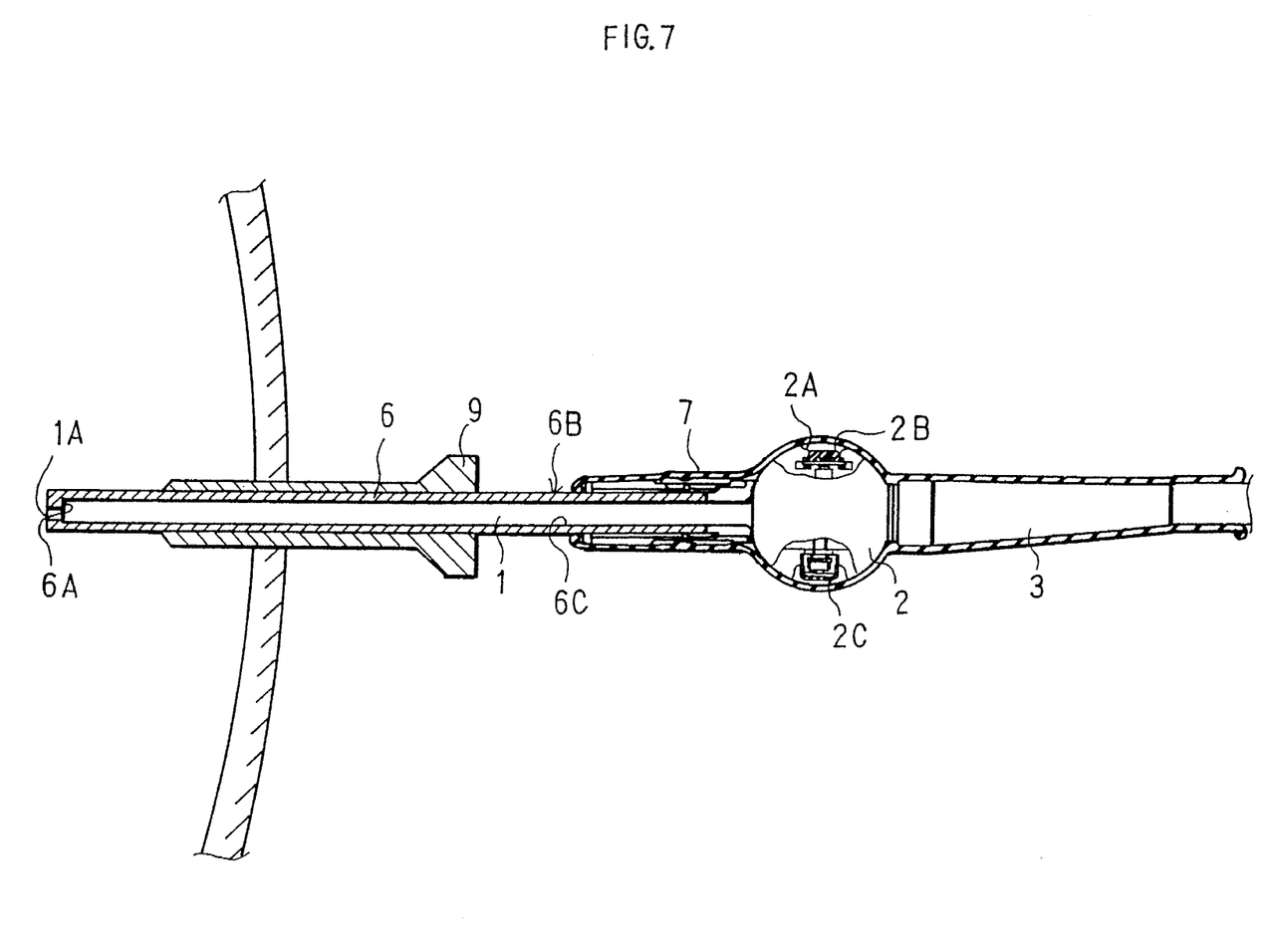
FIG. 7 is a sectional view of the essential portions of the hard endoscope on which the sheath according to the present invention is attached and which is inserted into the body cavity through a trocar.

FIG. 2 shows the hard endoscope assembly to the present invention. The hard endoscope assembly consists of a hard endoscope 4 comprising a hard insertion tube 1 which is to be inserted into the body cavity of a patient through a trocar 9 (see FIG. 7) to view the cavity inside or make necessary treatments therein, a controller 2 and a coupling tube 3. Hard insertion tube 1, controller 2 and coupling tube 3 are connected together to have a nearly linear form, and a sheath 8 consisting of a hard sheath member 6 and a soft sheath member 7 and which is to be used as fitted on the hard endoscope 4.
Hard endoscope 4:

The hard insertion tube 1 is designed for viewing a desired region in the body cavity of a patient. For use in endoscopy, first the hard sheath member 6 is fitted onto the hard insertion tube 1, then introduced into the trocar 9 and inserted very easily at the free end thereof into the body cavity such as abdomen. The hard insertion tube 1 is made of a metal, and has a smooth outer circumferential surface 6B worked like a mirror surface. Since all parts of the hard insertion tube 1 are covered with the hard sheath member 6 when in use, only the member 6 has to be sterilized or disinfected for a next use of the endoscope. Namely, the hard insertion tube 1 need not be washed to remove blood on it, sterilized at a high temperature sterilization nor immersed in a sterilizer. Such washing and sterilization are very troublesome in the busy daily clinical work.

The hard insertion tube 1 has formed in the end face thereof a window 1A through which the diseased region is viewed or otherwise treated. This window 1A is so formed that it is made, by locking means 10 (see FIGS. 5 and 6) provided between the controller 2 and hard sheath member which will be discussed in detail later, to precisely coincide with a window formed in the end face 6A of the hard sheath member 6.

The controller 2 is designated to have a spherical shape the center of which coincides with the axis of the hard insertion tube 1. The soft sheath member 7 is expansible and so can be fitted on the entire outer circumference of the controller 2 in a watertight manner. Holding the controller 2 in hand along with the attached soft sheath member 7, the operator can use it for various kinds of operation such as photography of the diseased region, air or water filling, etc. The controller 2 has a concavity 2A formed in a portion of the outer circumference thereof, in which control buttons 2B and 2C are so disposed as not to project out of the outer circumference. These control buttons 2B and 2C can be turned on and off as pressed by finger with only a small force from above the soft sheath member 7. The shape of the controller 2 is not limited only to the one described herein, but the controller 2 may be formed in any other shape without any sharp projections such as presents a smooth, curved profile, to which the soft sheath member 7 would be easily fitted.

Figure 5:
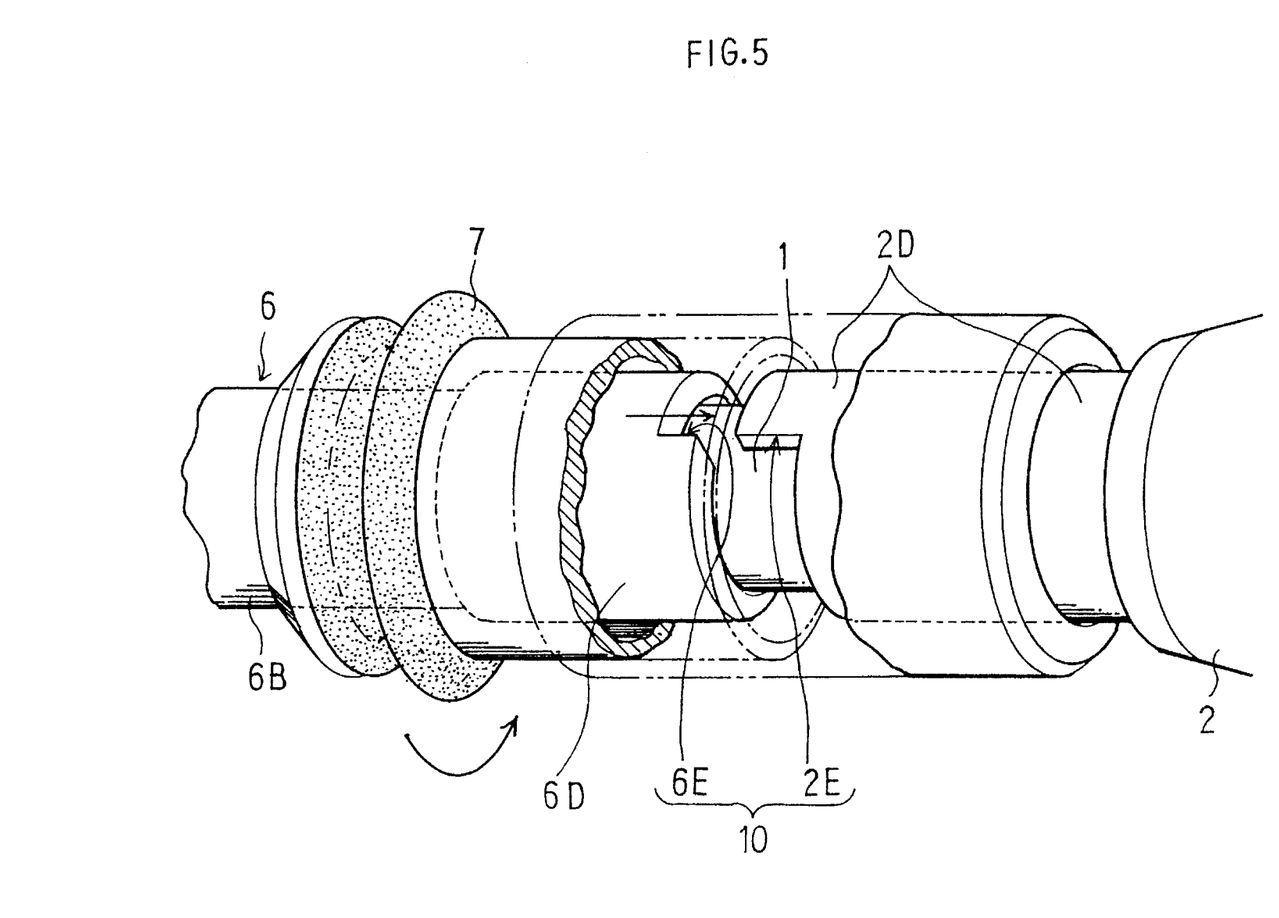
FIG. 5 is a fragmentary perspective view showing the locking means used in the head endoscope assembly in FIG. 2.

As shown in FIG. 5, the controller 2 is cut at 2E at the end portion 2D thereof adjacent to the hard sheath member 6. The cut 2E forms a part of the locking means 10 including another part (cut 6E of the end portion 6D of the hard sheath member 6, adjacent to the controller 2). These cuts 2E and 6E cooperate with each other to provide a precise circumferential positioning between the controller 2 and hard sheath member 6. This will also be discussed with reference to FIG. 5.

Figure 3:
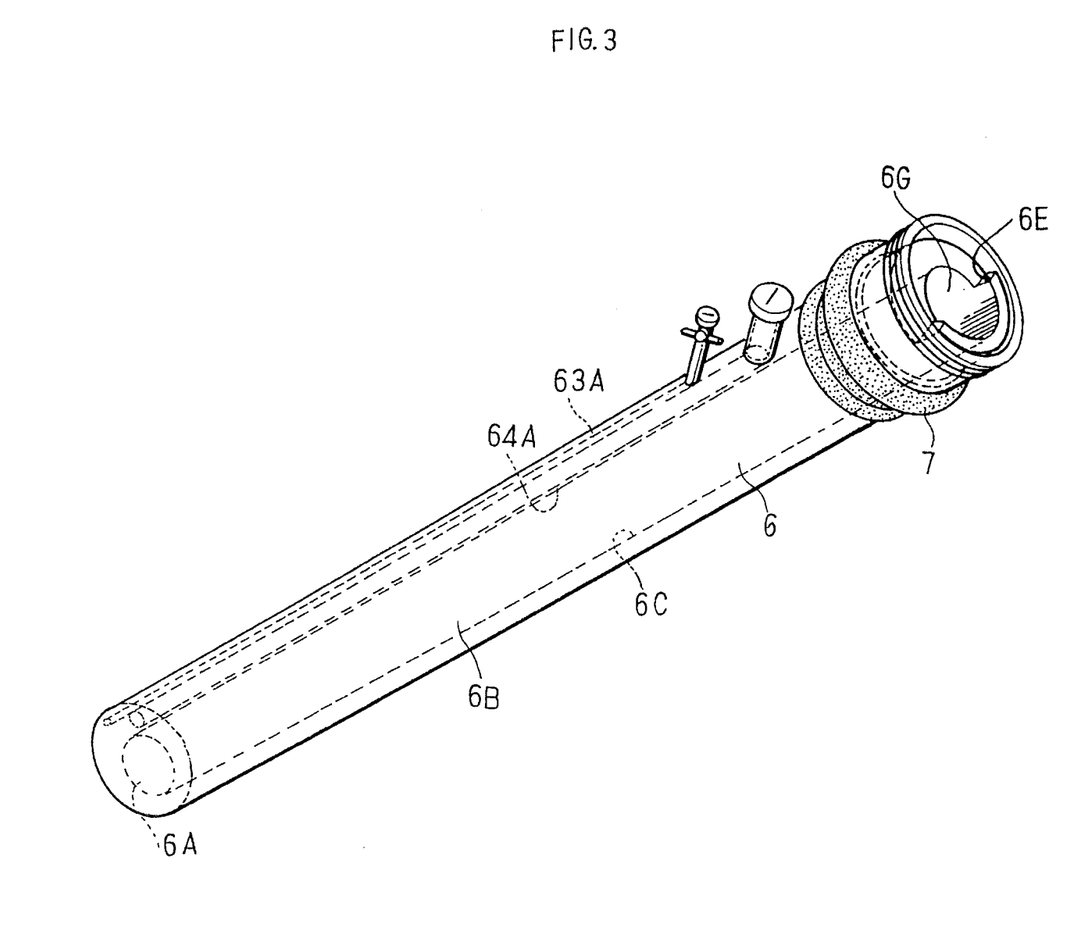
FIG. 3 is a perspective view of the sheath according to the present invention.

The coupling tube 3 is connected to the controller 2 in line with the latter in such a manner that its axis is generally aligned with the axis of the hard insertion tube 1. The coupling tube 3 is connected to an external apparatus (not shown) by means of a connector 5. It should be noted that the coupling tube 3 may not be precisely aligned with the controller 2 but its axis may be a little deviated from that of the controller 2.
Sheath 8:

The hard sheath member 6, a part of the sheath 8, made of a hard material which is not likely to be broken by a blade at the end of the trocar 9, such as stainless steel. As shown in FIG. 3, it is bottomed cylinder having an end face 6A at the bottom end thereof, outer circumference 6B and an insertion opening or bore (also inner circumferential surface) 6G at the other end thereof. The inner and outer circumferential surfaces 6C and 6B respectively are worked to be smooth like a mirror surface so that the hard insertion tube 1 can be smoothly inserted into the hard sheath member 6 and the latter can be also smoothly inserted into the trocar 9. The smoothness is such that the spaces between these pieces are airtight as well as watertight.

The bore 6G in the hard sheath member 6 in this embodiment has the axis thereof deviated from the axis of the hard insertion tube 1, and also has formed in the thickest-wall portion thereof passages such as an air/water passage 63A, forceps passage 64A, etc. as shown in FIG. 3.

Figure 4:
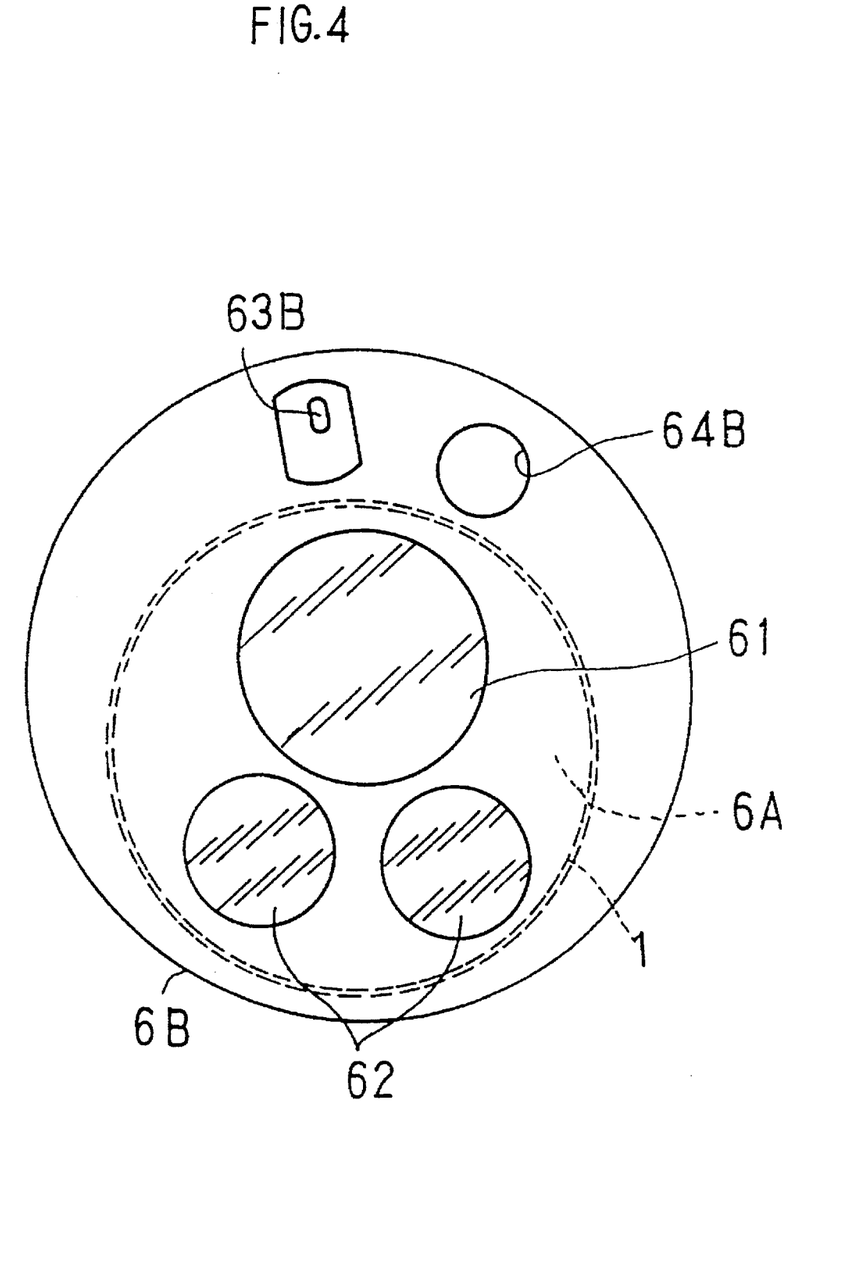
FIG. 4 is a bottom view of the sheath in FIG. 3.

As shown in FIG. 4, there are formed in the end face 6A of the hard sheath member 6 that faces the end face of the hard insertion tube 1 various windows such as viewing window 61, illumination windows 62, an air/water nozzle 63B intended for washing the viewing window or of for the like purpose, a forceps hole 64B through which a forceps (not shown) is led out to the diseased region and retreated or the like.

As shown in FIG. 5, the hard sheath member 6 has an end portion 6D cut at 6E. The cut 6E forms the other part of the locking means 10 (one part thereof is the cut 2E at the end portion 2D of the controller 2 as previously described). These cuts 2E and 6E are opposite to each other and closely about each other.

The soft sheath member 7 is removably fitted on the opening-side end portion of the hard sheath member 6 to ensure the airtightness and watertightness, and it is closely attachable over the controller 2. The soft sheath member 7 is made of an expansible material such as an elastomer. It is also made thin. Therefore, the control buttons or switches 2B and 2C in the controller 2 can be operated as pressed from above the soft sheath member 7. The soft sheath member 7 is used as e x t ended from the rolled state shown in FIG. 5, namely, it is unrolled and attached over a predetermined length of the hard endoscope. After use, the soft sheath member 7 is removed from the hard sheath member 6 and discarded. It is a disposable, not to be reused.

Figure 6:
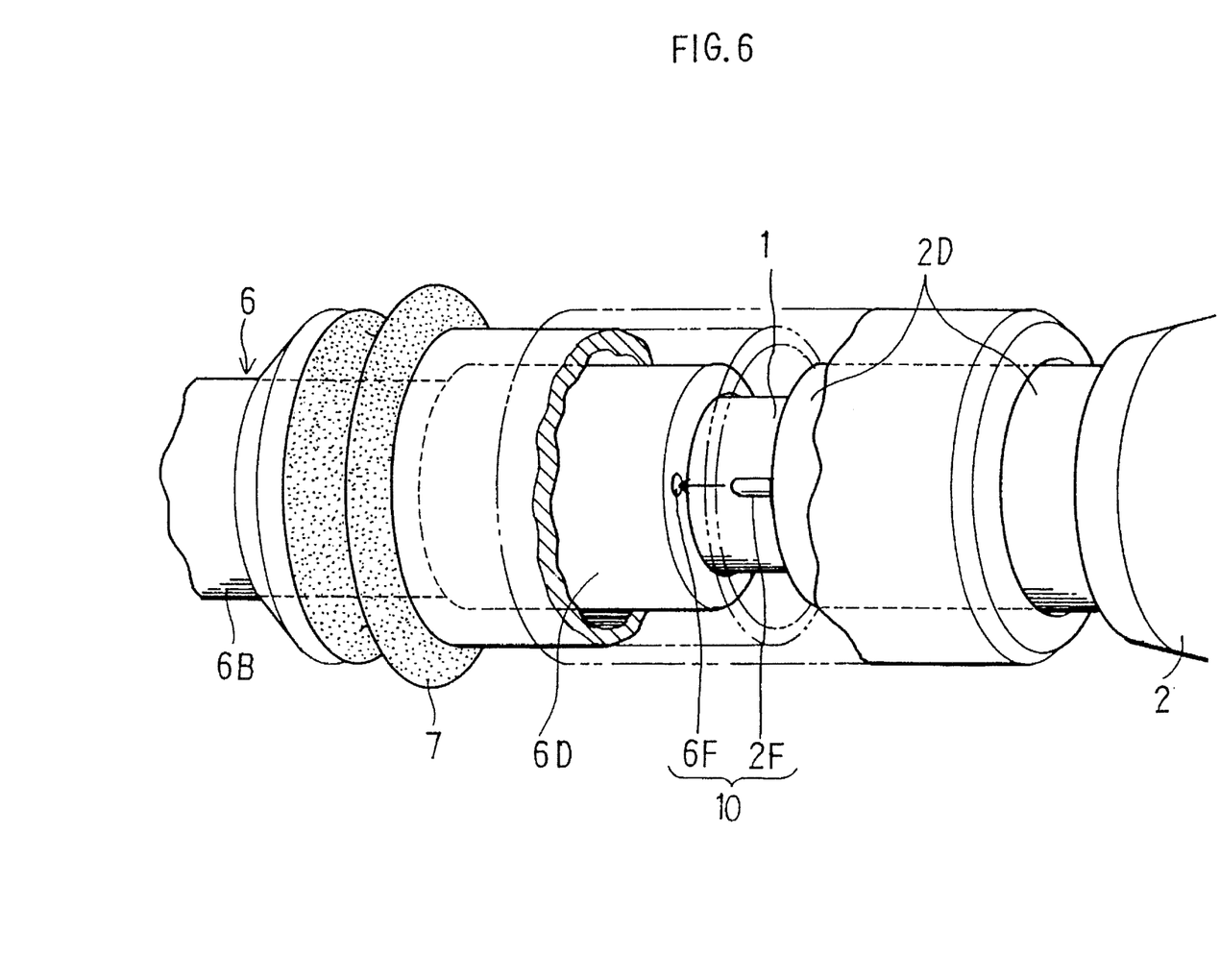
FIG. 6 is a fragmentary perspective view showing a variant of the locking means.

The locking means 10 consists of the pair of cuts 2E and 6E having been described above. These cuts 2E and 6E are formed, along a half of the circumference, at the end portions 2D and 6D, respectively. They are closely fitted to each other and serve as the locking means 10 to correctly position the hard sheath member 6 circumferentially of the hard endoscope. However, the locking means 10 is not limited to the pair of the cuts 2E and 6E alone but it may be formed from three or more sets of cuts, which complement each other. Also the locking means 10 may be formed from a pin 2F provided at the end portion 2D of the controller 2 and a hole 6F formed in the end portion of the hard sheath member 6, as shown in FIG. 6. When the locking means 10 is used, the pin 2F is inserted into the hole 6F.

According to this embodiment, the soft sheath member 7 can be attached on the controller 2 simply, smoothly and closely.

The control buttons 2B and 2C are provided at position one step lower than the outer surface of the controller 2. When the operator holds the controller 2 in hand from above the soft sheath member 7, the control buttons 2B and 2C will not be pressed by the operator's hand. So the control buttons will not possibly be turned on or off by mistake.

After the hard endoscope is used for a patient, the soft sheath member 7 is removed from the hard sheath member 6 and discarded, and the hard sheath member 6 is then sterilized or disinfected. For endoscopy with a next patient, a fresh soft sheath member 7 sterilized or disinfected beforehand has only to be attached place. Thus, no troublesome sterilization of the endoscope body is required.

As having been described in the foregoing, the coupling tube is not projected laterally from the controller, that is, perpendicularly thereto, as in the conventional endoscope, but it is extended nearly linearly from the controller. Also the control buttons are so provided in the controller as not to project out of the outer circumference of the controller. So the soft sheath member is smoothly fitted and attached on the controller, and the control buttons can be operated by finger from above the soft sheath member.

Also, when the controller is turned about the axis thereof, the coupling tube and any external apparatus connected to the coupling tube will not possibly be displaced correspondingly. Thus the hard endoscope according to the present invention has a better operability. The operator or doctor can devote himself to viewing of the diseased region or any other treatments. The portion of the hard endoscope that is likely to be contaminated with blood or the like can be entirely covered with the sheath to keep off such blood. Therefore, the hard endoscope according to the present invention is highly reliable.

In the hard endoscope according to the present invention, the locking means provided between the hard sheath member of the sheath and the controller or hard insertion tube of the hard endoscope permits to correctly portion the sheath circumferentially of the endoscope. Thus, the windows for viewing and other treatment, formed in the end face of the endoscope, can be aligned easily and correctly with those formed in the end face of the hard sheath member.

The nearly entire hard insertion tube of the hard endoscope can be inserted into the hard sheath member, of the sheath according to the present invention, of which both the inner and outer surface are very smooth, and the entire controller including the control buttons can be covered with the soft sheath member. Thus, the end portion of the hard endoscope, which would conventionally be likely to be contaminated due to the possible contact with the diseased region, adhesion of blood or con tact with the operator, can be fully covered with the sheath according to the present invention. So only the hard sheath member has to be simply sterilized or disinfected for a next use and it suffices to replace the used soft sheath member with a fresh one. Namely, the sterilization or disinfection of the hard endoscope body, which otherwise would take much labor and time, is not required. Thus, the endoscopy can be done very rapidly and efficiently with the hard endoscope according to the present invention.

What is claimed is:

1. A hard endoscope comprising:

a hard insertion tube which is to be inserted into a body cavity of a patient through a trocar;

a controller connected to the hard insertion tube;

a coupling tube for connection of an external apparatus;

a sheath including a hard sheath member and a soft sheath member;

the controller being of a shape free of sharp projections;

the controller, the hard insertion tube and the coupling tube having a nearly linear form when assembled together;

control buttons being disposed on the controller and recessed so as not to project from the outer surface of the controller;

the hard sheath member, having inner and outer surfaces which are smooth, being fitted on the hard insertion tube; and the soft sheath member being removably and hermetically sealed against the hard sheath member proximate the controller, extending therefrom to cover the controller so that the control buttons are operable from outside the soft sheath member.

2. A hard endoscope as set forth in claim 1, further comprising:

a means for positioning the sheath circumferentially of the endoscope between the hard sheath member and one of the controller and the hard insertion tube of the hard endoscope.

3. A sheath, for use as fitted on a hard endoscope having a hard insertion tube to be inserted into the body cavity of a patient through a trocar, a controller having a concavity in which control buttons are disposed so as not to project outwardly from a surface thereof, and a coupling tube for connection of an external apparatus, the tube, controller and coupling tube being disposed so as to have a generally linear form when assembled together, the sheath comprising:

a hard sheath and an expansible soft sheath;

the hard sheath member having the form of a bottomed cylinder, in which the insertion tube of the hard endoscope is to be inserted, the hard sheath member being made of a hard material, formed to have a constant outside diameter so that an airtightness can be maintained during insertion of the hard insertion tube into the trocar and having the inner and outer circumferential surfaces worked so as to be free from irregularity thereon;

an expansible soft sheath member removably attachable hermetically, proximate the open end of the hard sheath member, and fittable over the controller of the hard endoscope; and the soft sheath member including means for permitting depression of the control buttons from outside the soft sheath member.

4. A sheath as set forth in claim 3, wherein:

the soft sheath member is made of a thin, elastomeric material; and the soft sheath member is extendable from a rolled position to an unrolled position in which;t covers the controller.

5. A hard endoscope, comprising:

a hard insertion tube for insertion into a body cavity of a patient through a trocar;

a controller, connected at a first end thereof to the hard insertion tube, the controller being of a shape free of sharp projections;

control buttons, disposed on the controller, within recesses therein of sufficient depth to permit a contact surface of each of the control buttons to be one of flush with and below an outer surface of the controller;

a coupling tube for connection of an external apparatus connected to a second end of the controller opposite the first end;

a sheath including a hard sheath member and a soft sheath member;

the controller, the hard insertion tube and the coupling tube presenting a substantially linear form when assembled together;

the hard sheath member being open at one end for slidably receiving the hard insertion tube in a closely fitted manner;

the soft sheath member removably and hermetically fitted on a portion of the hard sheath member, proximate the one end, and extending therefrom to cover the controller; and the soft sheath member including means for permitting depression of the control buttons from outside the soft sheath member.

6. A hard endoscope as set forth in claim 5, wherein said controller is substantially spherical.

7. A hard endoscope as set forth in claim 5, further comprising means for circumferentially aligning the hard sheath member and hard insertion tube of the hard endoscope in a desired relative position.

8. A hard endoscope as set forth in claim 7, wherein the means for circumferentially aligning the hard sheath member and hard insertion tube are carried on the hard sheath member, and one of the controller and the hard insertion tube of the hard endoscope.

9. A hard endoscope, as set forth in claim 8, wherein:

the hard sheath and the controller have juxtaposed end surfaces; and the means for circumferentially aligning the hard sheath member and hard insertion tube include a pin extending from one of the juxtaposed end surfaces of the hard sheath member and the controller, and a hole for receiving the pin in a remaining one of the juxtaposed end surfaces.

10. A hard endoscope, as set forth in claim 8, wherein:

the hard sheath and the controller have juxtaposed end surfaces; and the means for circumferentially aligning the hard sheath member and hard insertion tube include cooperating means carried on each of juxtaposed end surfaces of the hard sheath member and the controller, the cooperating means comprising complementary interlocking shapes.

11. A sheath for a hard endoscope of the type having a hard insertion tube to be inserted into the body cavity of a patient through a trocar, a controller having a concavity in which control buttons are disposed so as not to outwardly project from a surface thereof, and a coupling tube for connection to an external apparatus, the tube, controller and coupling tube being disposed so as to have a generally linear form when assembled together, the sheath comprising:

a hard sheath member;

a soft sheath member;

the hard sheath member being substantially a length of the hard insertion tube and open at one end for slidably receiving the hard insertion tube in a closely fitted manner; and the soft sheath member being removably and hermetically fitted on a portion of the hard sheath member proximate the one end, and extendable therefrom to cover the controller; and the soft sheath member including means for permitting depression of the control buttons from outside the soft sheath member.

12. A sheath as set forth in claim 10, wherein:

the soft sheath member is made of a thin, elastomeric material; and the soft sheath member is extendable from a rolled position to an unrolled position in which it covers the controller.

\* \* \* \* \*